United States Patent [19]

Ishiwatari

[11] Patent Number: 6,123,955

[45] Date of Patent: Sep. 26, 2000

[54] COCKROACH REPELLENT

[75] Inventor: Takao Ishiwatari, Toyonaka, Japan

[73] Assignee: Sumitomo Chemical Company, Limited, Osaka, Japan

[21] Appl. No.: 09/112,138

[22] Filed: Jul. 9, 1998

[30] Foreign Application Priority Data

Nov. 18, 1997 [JP] Japan .................................. 9-317112

[51] Int. Cl.$^7$ .................................................. A01N 25/34
[52] U.S. Cl. ...................... 424/411; 424/403; 424/405; 424/409; 424/DIG. 10; 514/531; 514/919
[58] Field of Search .............................. 514/68, 74, 531, 514/919; 424/403, 405, 409, 411, 416, DIG. 10

[56] References Cited

U.S. PATENT DOCUMENTS

| | | | |
|---|---|---|---|
| 3,295,246 | 1/1967 | Landsman et al. | ........................ 43/131 |
| 3,655,129 | 4/1972 | Seiner | ........................ 239/60 |
| 4,160,335 | 7/1979 | Von Komorn et al. | .................... 43/131 |
| 4,889,872 | 12/1989 | Naumann et al. | . |

FOREIGN PATENT DOCUMENTS

| | | |
|---|---|---|
| 0576270 | 12/1993 | European Pat. Off. . |
| 8231321 | 9/1996 | Japan . |

*Primary Examiner*—Neil S. Levy
*Attorney, Agent, or Firm*—Stevens, Davis, Miller & Mosher, L.L.P.

[57] ABSTRACT

A cockroach repellent comprising 2,3,5,6-tetrafluorobenzyl (1R)-trans-3-(2,2-dichlorovinyl)-2,2-dimethylcyclopropanecarboxylate {transfluthrin} as its active ingredient and a method for repelling cockroaches by using transfluthrin.

4 Claims, No Drawings

COCKROACH REPELLENT

FIELD OF THE INVENTION

The present invention relates to cockroach repellents.

BACKGROUND ART(S)

Hitherto, an aerosol formulation containing N,N-diethyl-m-toluamide was utilized in order to repel mosquitoes and gnats. Furthermore, it is described in Japanese Laid-open patent No. sho-56-92803A that cockroaches can be repelled by utilizing ether compounds such as empenthrin and the like.

Noxious pest repellents containing N,N-diethyl-m-toluamide were developed to target mosquitoes and gnats, but were not sufficient to repel cockroaches effectively. Furthermore, the ether compounds described in Japanese laid-open patent No. sho-56-92803A are very effective for some moments after disposal, but with the effectiveness of the repellent to greatly decrease together with the passing of time, are not sufficient to repel cockroaches.

DISCLOSURE OF THE INVENTION

The present invention is, something that was provided as a high activity cockroach repellent as well as a cockroach repellent method, a cockroach repellent containing transfluthrin [2,3,5,6-tetrafluorobenzyl (1R)-trans-3-(2,2-dichlorovinyl)-2,2-dimethylcyclopropanecarboxylate as an active ingredient, a cockroach repellent method using transfluthrin, especially, a cockroach repellent method using a sheet having transfluthrin set indoors.

Transfluthrin used in the present invention, a compound described in U.S. Pat. No. 4,889,872, can be produced by complying to the report of said U.S. patent.

The cockroach repellent of the present invention may be the active ingredient of transfluthrin itself, but the form wherein transfluthrin is supported with any carrier is standard, for example, taking a sheet form for formulation. Formulations to be kneaded to the resin, emulsifiable concentrates, oil formulations, wettable powders, flowables, granules, dusts, aerosol formulations and formulations for heat vaporization are shown as possible forms, and using transfluthrin supported on a sheet is especially preferred.

In the situation where the cockroach repellent of the present invention takes a form of sheet formulation, the material for said sheet is not especially limited, and for example, paper, synthetic resin (e.g. polyethylene, cross-linked polyethylene, polypropylene, cellophane, polyvinylidene chloride, polyvinyl chloride, polyester, polyvinyl acetal, polyamide, fluorocarbon resin, polycarbonate, copolymers thereof, etc.) and cloth (e.g. cotton, silk, wool, hemp, synthetic fibers, etc.) are feasible. The amount of transfluthrin to be supported on the sheet, standardly is about 0.01 g to 50 g for 1 $m^2$, preferably 0.05 g to 20 g.

In the situation where the cockroach repellent of the present invention takes a form of emulsifiable concentrates, oil formulations or the like, the amount of transfluthrin within said formulation, has 0.01 to 10% by weight as standard.

Furthermore, the cockroach repellent of the present invention may additionally contain pest repellent ingredients other than transfluthrin, for example, N,N diethyl-m-toluamide, carane-3,4-diol, 1-methylpropyl 2-(2-hydoxyethyl)-1-piperidinecarboxylate, p-menthane-3,8-diol, botanical essential oils having pest repellency, etc.

The cockroach repellent of the present invention may be used in the location desired for cockroach control, for example, sites intruded by cockroaches such as household, warehouse, food service areas etc. as that utilization situation.

As a cockroach repellent method of the present invention; not only does the cockroach repellent formulation of the present invention simply employ steps of setting such as dispersing, spraying, spreading, placing or pasting, but wherein the transfluthrin is preserved in the materials of household instrument ingredients beforehand by spreading, soaking, kneading, dripping, and the like manner, so that using household instruments that were built from using said household instrument ingredients are also methods included. The amount of transfluthrin used in the cockroach repellent of the present invention, generally for 1 $m^2$ is about 0.01 g to 50 g, but preferably 0.05 to 20 g.

The cockroach repellent of the present invention is effective in repelling various cockroaches such as German cockroach (*Blattella germanica*), smokybrown cockroach (*Periplaneta fuliginosa*), American cockroach (*Periplaneta americana*), brown cockroach (*Periplaneta brunnea*) and oriental cockroach (*Blatta orientalis*).

EXAMPLES

On 6 cm×9 cm filter paper 1.0 mL of an acetone solution (1% by weight) of transfluthrin was spread, then dried for the gained cockroach repellent (sheet formulation) to be folded, as to be a tube-like triangular pillar where one side of the triangle-shaped base was 3 cm.

In a 650 mL volume plastic cup said triangular pillar was placed as a shelter (cockroach hiding residence), 10 adult German cockroaches (*Blattella germanica*) were placed in said plastic cup together with food and water, and then observed the number of cockroaches in the shelter 24 hours later. The test was repeated twice. Furthermore, the same test was performed wherein said triangularly pillared shelter conserving conditions of 25° C., 60% humidity for 1 month was used. Results are stated in Table 1. The results are evaluated by the number of cockroaches inside the shelter. Namely, the "−" means that was 0, "+" is for 1 to 2 cockroaches, and "++" is 3 or more.

In addition, tests results using empenthrin and furthermore N,N-diethyl-m-toluamide (Deet) replacing transfluthrin as well as test results using an untreated shelter are included to be stated in Table 1.

TABLE 1

|  | Test results just after treatment | Test results after 1 month conserved |
| --- | --- | --- |
| transfluthrin | − | − |
| empenthrin | − | ++ |
| Deet | ++ |  |
| non-treatment | ++ |  |

As seen in the above table, the cockroach repellent of the present invention can be effective for repelling cockroaches even after a placing of 1 month.

The cockroach repellent of the present invention, together with an early term effectiveness as well as a long term continuing effectiveness is an extraordinary repellent.

What is claimed is:

1. A method for repelling cockroaches which comprises applying an effective amount for repelling cockroaches of transfluthrin to sites intruded by cockroaches.

2. A method for repelling cockroaches which comprises setting a sheet having transfluthrin indoors.

3. A method according to claim 2, wherein the sheet contains 0.01 g to 50 g per 1 $m^2$.

4. A method according to claim 2, wherein the sheet contains 0.05g to 20 g per 1 $m^2$.

* * * * *